(12) United States Patent
Weichold et al.

(10) Patent No.: US 7,887,825 B2
(45) Date of Patent: Feb. 15, 2011

(54) EMULSIFIER COMPOSITION BASED ON PENTAERYTHRITOL ESTERS AND ALKOXYLATED NONIONIC EMULSIFIERS

(75) Inventors: Catherine Weichold, Düsseldorf (DE); Helga Gondek, Düsseldorf (DE); Ulrich Issberner, Ambler, PA (US); Rolf Kawa, Monheim (DE); Caroline Goget, Paris (FR)

(73) Assignee: Cognis IP Management GmbH, Duesseldorf (DE)

( * ) Notice: Subject to any disclaimer, the term of this patent is extended or adjusted under 35 U.S.C. 154(b) by 227 days.

(21) Appl. No.: 11/908,310

(22) PCT Filed: Mar. 2, 2006

(86) PCT No.: PCT/EP2006/001897

§ 371 (c)(1),
(2), (4) Date: Sep. 11, 2007

(87) PCT Pub. No.: WO2006/094701

PCT Pub. Date: Sep. 14, 2006

(65) Prior Publication Data

US 2008/0166381 A1 Jul. 10, 2008

(30) Foreign Application Priority Data

Mar. 11, 2005 (DE) .................. 10 2005 011 334

(51) Int. Cl.
*A61K 8/02* (2006.01)
*A01N 25/34* (2006.01)

(52) U.S. Cl. ...................... 424/401; 424/402
(58) Field of Classification Search ............... 514/539
See application file for complete search history.

(56) References Cited

U.S. PATENT DOCUMENTS

| | | | |
|---|---|---|---|
| 5,705,169 A | 1/1998 | Stein et al. | |
| 5,730,960 A | 3/1998 | Stein et al. | |
| 5,945,091 A | 8/1999 | Habeck et al. | |
| 6,193,960 B1 | 2/2001 | Metzger et al. | |
| 6,277,430 B1 * | 8/2001 | Cain et al. | 426/601 |
| 6,576,678 B1 * | 6/2003 | Bruening et al. | 516/22 |
| 6,623,746 B1 * | 9/2003 | Wadle et al. | 424/402 |
| 6,927,241 B2 * | 8/2005 | Ansmann et al. | 516/77 |
| 2002/0045670 A1 * | 4/2002 | Lorant | 516/8.1 |
| 2005/0079141 A1 * | 4/2005 | Zander et al. | 424/59 |
| 2006/0039956 A1 * | 2/2006 | Hensen et al. | 424/443 |

FOREIGN PATENT DOCUMENTS

| | | |
|---|---|---|
| DE | 197 12 033 | 9/1998 |
| DE | 199 50 017 | 4/2001 |
| DE | 100 25 671 | 12/2001 |
| EP | 0 179 416 | 4/1986 |
| EP | 0 693 471 | 1/1996 |
| EP | 0 694 521 | 1/1996 |
| EP | 0 818 450 | 1/1998 |
| WO | WO 03/037293 | 5/2003 |

OTHER PUBLICATIONS

Brandner et al., "Relative Esterifiability of the Primary and Secondary Hydroxyl Groups of Glycerol", J. Am. Oil Chem. Soc., vol. 37, 1960, pp. 390-396.
Randner et al., "The Equilibrium Distribution of Acyl Groups Between Primary and Secondary Hydroxyl Positions in Partial Esters", J. Am. Oil Chem. Soc., vol. 41, 1964, pp. 367-370.
Herbert P. Fiedler, Lexikon Der Hilfsstoffe Fuer Pharmazie, Kosmetik und Angrenzende Gebiete, Der pharmazeutische Betrieg, Band 9, 1971, pp. 265-270.
Kirk-Othmer, Encyclopedia of Chemical Technology, "Emulsions", vol. 8, 1979, pp. 909-918.
Hugo Janistyn, Handbuch Der Kosmetika und Riechstoffe, Band 1, p. 470.
Hugo Janistyn, Handbuch Der Kosmetika und Riechstoffe, Band 3, pp. 68-78.
P. Finkel, "Formulierung kosmetischer Sonnenschutzmittel", SÖFW Journal, vol. 122, 1996, p. 543-546, 548.
P. Finkel, "Formulierung kosmetischer Sonnenschutzmittel", Parf. und Kosmetik, vol. 3, 1999, pp. 10-12, 14-16.
Kosmetikverordnung, Appendix 6, parts A and B.

* cited by examiner

*Primary Examiner*—Sreeni Padmanabhan
*Assistant Examiner*—Timothy E Betton
(74) *Attorney, Agent, or Firm*—Fox Rothschild LLP

(57) ABSTRACT

An emulsifier composition including an ester selected from the group consisting of: pentaerythritol, dipentaerythritol, tripentaerythritol, and mixtures thereof; at least one alkoxylated nonionic emulsifier; and less than 10% by weight water, where partial glycerides may be present in an amount of less than 10% by weight, based on the amount of component (a) present in the composition, is provided. A process for the production of an emulsion, including dispersing the emulsifier composition in an oil phase; heating the emulsifier composition dispersed in the oil phase to a temperature above the phase inversion temperature thereof; heating an aqueous phase to a temperature above the phase inversion temperature thereof; and stirring the oil phase with the aqueous phase and cooling to room temperature is also provided. A cosmetic composition including the emulsifier composition is also provided.

20 Claims, No Drawings

Page 1 of US 7,887,825 B2 …

EMULSIFIER COMPOSITION BASED ON PENTAERYTHRITOL ESTERS AND ALKOXYLATED NONIONIC EMULSIFIERS

CROSS-REFERENCE TO RELATED APPLICATIONS

This application is a national phase filing under 35 U.S.C. §371 and claims priority to International Application No. PCT/EP2006/001897 which has an International filing date of Mar. 2, 2006, and which designated the United States of America and which claims priority to German Application No. 10 2005 011 334.6, filed Mar. 11, 2005, the entire disclosures of which are hereby incorporated herein by reference.

FIELD OF THE INVENTION

This invention relates generally to special emulsifier compositions, and more particularly, emulsifier compositions based on esters of pentaerythritol or oligomers of pentaerythritol and alkoxylated nonionic emulsifiers. The invention also relates to the use of these emulsifier compositions for the production of emulsions and to cosmetic formulations including the emulsifier compositions.

BACKGROUND INFORMATION

Various waxes are available to the expert for the production of cosmetic and/or pharmaceutical formulations, acting both as consistency factors—particularly by building up lamellar structures—and as co-emulsifiers.

In formulations produced by the PIT process (PIT=phase inversion temperature), mono-/di-/triglyceride mixtures are commonly used as co-emulsifiers. The mono-/di-/triglyceride ratio and the emulsifier/co-emulsifier ratio have to be carefully adapted for this particular application. In DE 100 25 671 A1 for example, it is emphasized that the monoglyceride content must not fall below a certain value in order to obtain particularly fine-particle emulsions which are stable in storage and do not gel, even under temperature stress. This means that narrow limits have to be observed for the production of emulsifier compositions for PIT emulsions based on glycerides. However, this is not without production-related problems. Even in long-term storage, the ratio of the mono-, di- and triglycerides to one another can change.

Formulations produced by the PIT process are generally distinguished by a particularly fine droplet distribution and good stability. However, where mono- and diesters of glycerol are used as co-emulsifiers, inter- and intramolecular migration can occur. In this event, a 1-acyl glyceride mixture, for example, isomerizes into a mixture of 1- and 2-acyl glycerides or disproportionation to glycerol and the diglycerides 1,2-diacyl and 1,3-diacyl glyceride and the corresponding triglyceride occurs (cf. J. D. Brandner, R. L. Birkmeier, *J. Am. Oil Chem. Soc.* 1960, 37, 390-396; J. D. Brandner, R. L. Birkmeier, *J. Am. Oil Chem. Soc.* 1964, 41, 367-370). The scale of these isomerization and disproportionation reactions is time- and temperature-dependent and, in addition, can also depend on the catalyst used for the production of the glycerides. The phenomenon of acyl migration in glycerides complicates their selective synthesis and also influences their applicational properties. Emulsifier mixtures which contain partial glycerides as co-emulsifiers and which are used for the production of PIT emulsions often show hugely varying properties from batch to batch, so that reproducibility of the final formulation cannot always be guaranteed.

There remains a need to provide emulsifier compositions which can be used in a broad mixing ratio, are suitable in particular for the production of PIT emulsions and are not attended by the problems observed with partial glycerides as so-emulsifiers. There also remains a need to provide emulsifier compositions which are suitable for the production of PIT and microemulsions having a particle size of 1000 nm or smaller.

SUMMARY OF THE INVENTION

Briefly described, according to an aspect of the invention, an emulsifier composition includes (a) an ester selected from the group consisting of: pentaerythritol, dipentaerythritol, tripentaerythritol, and mixtures thereof; (b) at least one alkoxylated nonionic emulsifier; and (c) less than 10% by weight water, where partial glycerides may be present in an amount of less than 10% by weight, based on the amount of component (a) present in the composition. The emulsifier composition may be incorporated into a phase inversion temperature (PIT) emulsion or a microemulsion, for producing an emulsion with a mean droplet size distribution of not more than 1000 nm.

According to another aspect of the invention, a process for the production of an emulsion includes the steps of: (i) providing an emulsifier composition, including: (a) an ester selected from the group consisting of: pentaerythritol, dipentaerythritol, tripentaerythritol, and mixtures thereof; (b) at least one alkoxylated nonionic emulsifier; and (c) less than 10% by weight water, where partial glycerides may be present in an amount of less than 10% by weight, based on the amount of component (a) present in the composition; (ii) dispersing the emulsifier composition in an oil phase; (iii) heating the emulsifier composition dispersed in the oil phase to a temperature above the phase inversion temperature thereof; (iv) heating an aqueous phase to a temperature above the phase inversion temperature thereof; and (v) stirring the oil phase with the aqueous phase and cooling to room temperature.

According to yet another aspect of the invention, a cosmetic composition includes an emulsifier composition, including: (a) an ester selected from the group consisting of: pentaerythritol, dipentaerythritol, tripentaerythritol, and mixtures thereof; (b) at least one alkoxylated nonionic emulsifier; and (c) less than 10% by weight water, where partial glycerides may be present in an amount of less than 10% by weight, based on the amount of component (a) present in the emulsifier composition, and where the emulsifier composition is present in the cosmetic composition in an amount of from about 0.5 to about 40% by weight of the cosmetic composition. The cosmetic composition may be coated onto a substrate, including nonwovens, woven fabrics, cosmetic wipes, and household wipes.

DETAILED DESCRIPTION OF THE INVENTION

The present invention relates to an emulsifier composition containing (a) at least one ester of pentaerythritol, dipentaerythritol, tripentaerythritol or a mixture of these esters, (b) at least one alkoxylated nonionic emulsifier and (c) less than 10% by weight water, characterized in that, if this composition contains partial glycerides, they are present in a quantity of, or less than, 10% by weight, based on the quantity of pentaerythritol ester (a).

In a preferred embodiment of the invention, the emulsifier composition contains partial glycerides in a quantity of, or less than, 8% by weight, preferably in a quantity of, or less than, 5% by weight, more preferably in a quantity of, or less than, 3% by weight and most preferably in a quantity of, or less than, 1% by weight, based on the quantity of pentaerythritol ester (a). In a preferred embodiment of the invention, the emulsifier composition does not contain any partial glycerides. In another embodiment of the present invention, the emulsifier composition contains 1 to 10% by weight, preferably 1 to 8% by weight, more preferably 1 to 5% by weight and most preferably 1 to 3% by weight partial glycerides, based on the quantity of pentaerythritol ester (a).

The terms emulsifier composition, emulsifier compound and compound are used synonymously.

The emulsifier composition according to the invention contains less than 5% by weight water, preferably less than 1% by weight water, more preferably less than 0.5% by weight water and most preferably less than 0.1% by weight water. Typically, the emulsifier compositions contain only the residual amounts of water from the raw materials used. The emulsifier composition preferably consists essentially of components (a), (b) and (c), the only impurities present emanating from the raw materials used.

The use of the compounds according to the invention enables PIT emulsions to be produced in a reproducible manner from batch to batch. By comparison with emulsifier compounds, such as Emulgade® SE-PF, the compound according to the invention essentially contains only two constituents. This means "fewer variables" for industrial-scale production and hence fewer uncertainty factors through raw material variations, so that better reproducibility and easier handling are guaranteed. In addition, where the emulsifier composition according to the invention is used, there is generally no need for optimization in the production of the final formulations where the concentration of alkoxylated emulsifiers, for example, often has to be further adapted. In addition, more stable PIT formulations—compared with known PIT formulations—can often be obtained with the compound according to the invention.

In contrast to the glycerides, virtually no disproportionations are observed, particularly for the esters of pentaerythritol with identical acyl groups, and isomerizations lead to the same product by virtue of the high symmetry of the molecule. Accordingly, the problems observed with glycerides do not arise with these esters.

Stability problems were observed when certain oil components, such as for example Eutanol® G16 and Eutanol® G (Guerbet alcohols), Cetiol® PGL (containing Guerbet alcohol) and Myritol 331, are used in PIT formulations. Accordingly, in known PIT formulations containing these oil components, at most one fifth of the total quantity of oil could consist of these oils. With the emulsifier composition according to the invention, the concentration of these "problem oils" could be increased by 25 to 50% by weight, based on the oil phase.

The use of the emulsifier composition according to the invention also affords distinct sensory advantages, i.e. it is possible to produce richer sprayable formulations which give better results from distribution on the skin via absorption to the final skin feel (parameters: stickiness, smoothness, oiliness, waxiness, softness) and which lead to higher acceptance.

Component (a)

According to the invention, preferred emulsifier compositions are characterized in that component (a) is selected from the group of C6-C22 fatty acid esters of pentaerythritol, dipentaerythritol, tripentaerythritol or a mixture of these esters which have a melting point of at least 30° C.

The esters may contain a single type of fatty acid acyl groups or a mixture of different fatty acid acyl groups. The fatty acids may be branched or unbranched and/or saturated or unsaturated. Fatty acids/fatty acid mixtures with a high content of saturated, unbranched fatty acids, particularly those emanating from vegetable raw material sources, are preferably used for the esterification. C14-C24 fatty acids and particularly C14-C20 fatty acids are preferred for the purposes of the invention. These fatty acids include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid. A particularly preferred embodiment contains esters of pentaerythritol, dipentaerythritol or tripentaerythritol containing less than 0.3% by weight C17 fatty acid acyl groups as component (a).

Another preferred embodiment of the emulsifier composition according to the invention is characterized in that component (a) is a pentaerythritol ester mixture with a percentage content of (i) 5 to 35% by weight monoester, (ii) 20 to 50% by weight diester and (iii) 25 to 50% by weight triester and optionally tetraester. A particularly preferred embodiment is characterized by a content of (a) 10 to 25% by weight monoester, (b) 25 to 40% by weight diester and (c) 30 to 45% by weight triester and optionally tetraester. A content of (a) 12 to 19% by weight monoester, (b) 25 to 35% by weight diester, (c) 30 to 40% by weight triester and (d) 6 to 11% by weight tetraester is most particularly preferred.

Another preferred embodiment of the emulsifier composition according to the invention is characterized in that component (a) is obtained by esterification with a fatty acid mixture containing 40 to 50% by weight C16 fatty acid and 45 to 55% by weight C18 fatty acid. The rest of the fatty acid mixture consists of relatively short-chain (≦C14) and relatively long-chain (>C18) fatty acids. These esters are superior in regard to sensory properties. An ester of pentaerythritol which is obtained by reaction of pentaerythritol with a fatty acid mixture containing 42 to 48% by weight C16 fatty acid and 50 to 56% by weight C18 fatty acid (rest: ≦C14 and >C18 fatty acids) and which has the following ester distribution: 12 to 19% by weight monoester, (b) 25 to 35% by weight diester, (c) 30 to 40% by weight triester and (d) 6 to 11% by weight tetraester, is particularly preferred for the purposes of the invention. 1.8 to 2.2 mol of the fatty acid mixture per mol pentaerythritol is normally used for the esterification, a quantity of 1.9 to 2.1 mol being preferred.

For example, C16/C18 fatty acid/pentaerythritol esters can be produced by using—per mol pentaerythritol—1.8 to 2.2 mol and preferably 1.9 to 2.1 mol of a fatty acid mixture containing 40 to 50% by weight C16 fatty acid and 45 to 55% by weight C18 fatty acid of a raw material mixture with a corresponding fatty acid distribution and (a) carrying out the esterification in an inert gas atmosphere at temperatures of 180 to 250° C. and in the absence of solvents, (b) distilling of the water formed, (c) stirring the reaction mixture obtained in vacuo until an acid value of <1 and an OH value of 145 to 158 are reached, (d) filtering off unreacted pentaerythritol and (e) optionally applying an aftertreatment with hydrogen peroxide. The methods for monitoring and adjusting the acid value and the OH value are well known to the expert so that there is no need for further discussion here.

One embodiment of the emulsifier composition according to the invention is characterized in that component (a) is a dipentaerythritol ester mixture with a percentage content of (i) 5 to 35% by weight monoester, (ii) 20 to 50% by weight diester and (iii) 25 to 50% by weight triester and optionally tetraester. A particularly preferred embodiment is characterized by a content of (a) 10 to 25% by weight monoester, (b) 25 to 40% by weight diester and (c) 30 to 45% by weight triester and optionally tetraester. A content of (a) 12 to 19% by weight monoester, (b) 25 to 35% by weight diester, (c) 30 to 40% by weight triester and (d) 6 to 11% by weight tetraester is most particularly preferred.

Another embodiment of the emulsifier composition according to the invention is characterized in that component (a) is a tripentaerythritol ester mixture with a percentage content of (i) 5 to 35% by weight monoester, (ii) 20 to 50% by weight diester and (iii) 25 to 50% by weight triester and optionally tetraester. A particularly preferred embodiment is characterized by a content of (a) 10 to 25% by weight monoester, (b) 25 to 40% by weight diester and (c) 30 to 45% by weight triester and optionally tetraester. A content of (a) 12 to 19% by weight monoester, (b) 25 to 35% by weight diester, (c) 30 to 40% by weight triester and (d) 6 to 11% by weight tetraester is most particularly preferred.

The invention also encompasses mixtures of the above-mentioned esters of pentaerythritol, dipentaerythritol and tripentaerythritol.

Component (b)

In principle, nonionic alkoxylated emulsifiers, preferably with an Hydrophilic-Lipophilic Balance (HLB) value of 10 to 20, may be used as component (b). These include nonionic ethoxylated and propoxylated emulsifiers.

Detailed lists of the HLB values of commercially available emulsifiers are known to the expert and can be found, for example, in Fiedler, Lexikon der Hilfsstoffe für Pharmazie, Kosmetik und angrenzende Gebiete, Vol. 9, 1971, pages 265-270; Kirk-Othmer (3$^{rd}$ Edition), Vol. 8, pages 909-918 and Janistyn (3$^{rd}$ Edition), Vol. 1, page 470; and Vol. 3, pages 68-78. The anionic and nonionic emulsifiers with an HLB value above 10 listed there are intended to be part of the present disclosure. The emulsifiers may be used as the active substance or in the form of aqueous solutions.

The group of particularly suitable nonionic emulsifiers/surfactants with an HLB value >10 includes corresponding compounds selected from (1) products of the addition of ethylene oxide and/or propylene oxide onto linear and branched $C_{8-40}$ fatty alcohols, onto linear and branched $C_{12-40}$ fatty acids and onto alkylphenols with 8 to 15 carbon atoms in the alkyl group;

(2) $C_{12/18}$ fatty acid mono- and diesters of addition products of ethylene oxide and/or propylene oxide onto glycerol;

(3) ethylene oxide and/or propylene oxide addition products onto glycerol mono- and diesters and sorbitan mono- and diesters of saturated and unsaturated $C_{6-}$ fatty acids;

(4) ethoxylated and propoxylated alkyl mono- and oligoglycosides with 8 to 22 carbon atoms in the alkyl chain;

(5) products of the addition of ethylene oxide and/or propylene oxide onto castor oil and/or hydrogenated castor oil.

Individual examples (cf. Kirk-Othmer) of nonionic emulsifiers/surfactants with an HLB value of at least 10 are POE (5) sorbitan monooleate (POE=polyoxyethylene; PEG=polyethylene glycol), POE (40) sorbitol hexaoleate, PEG 400 dilaurate, POE (5) nonylphenol(ether), POE (20) sorbitan tristearate, POP/POE condensate, POE (6) nonylphenol(ether), POE (20) lanolin (ether und ester), POE (20) sorbitan trioleate, POE (8) stearic acid (monoester), POE (50) sorbitol hexaoleate, POE (6) tridecyl alcohol (ether), PEG 400 monostearate, POE (8) nonylphenol (ether), POE (10) stearyl alcohol (ether), POE (8) tridecyl alcohol (ether), POE (8) lauric acid (monoester), POE (10) cetylalcohol (ether), acetylated POE (10) lanolin, POE (20) glycerol monostearate, PEG 400 monolaurate, POE (16) lanolin alcohol (ether), POE (4) sorbitan monolaurate, POE (10) nonylphenol (ether), POE (15) long oil fatty acids (esters), POE (10) octylphenol (ether), PEG 600 monostearate, tertiary amines: POE fatty amines; POE (24) cholesterol, POE (14) nonylphenol (ether), POE (12) laurylalcohol, POE (20) sorbitan monostearate, sucrose monolaurate, POE (20) sorbitan monooleate, acetylated POE (9) lanolin, POE (20) stearyl alcohol, POE (20) oleyl alcohol (ether), PEG 1000 monooleate, POE (20) tallow amine, POE (20) sorbitan monopalmitate, POE (20) cetyl alcohol (ether), POE (25) propylene glycol monostearate, POE (20) nonylphenol (ether), PEG (1000) monolaurate, POE (20) sorbitan monolaurate, POE (23) lauryl alcohol (ether), POE (40) stearic acid (monoester), POE (50) lanolin (ether and ester), POE (25) soya sterol, POE (30) nonylphenol (ether), PEG 4000 distearate, POE (50) stearic acid (monoester), POE (70) dinonylphenol (ether), POE (20) castor oil (ether, ester), N-cetyl-N-ethyl-morpholinium ethyl sulfate, etc.

A preferred embodiment of the emulsifier composition according to the invention is characterized in that the alkoxylated nonionic emulsifier (b) is selected from the group of ethoxylated nonionic emulsifiers, preferably from the group of C12-C24 fatty alcohol ethoxylates or a mixture of C12-C24 fatty alcohol ethoxylates.

The C12-24 fatty acid ethoxylates in question preferably have an HLB value of at least 10, C16-C22 fatty acid ethoxylates being particularly preferred. These include, for example, Ceteareth-12, Ceteareth-20, Ceteareth-30, which are marketed by Cognis Deutschland GmbH & Co. KG under the names of Eumulgin® B1, Eumulgin® B2 and Eumulgin® B3 and Beheneth-10 (Eumulgin® BA 10) and Beheneth-25 (Eumulgin® BA 25).

In another preferred embodiment of the emulsifier composition according to the invention, the ratio by weight of (a) to (b) varies from 20:80 to 80:20, preferably from 25:75 to 75:25, more preferably from 40:60 to 60:40 and most preferably from 35:65 to 65:35. In this composition, particularly stable and fine-particle emulsions are obtained.

Commercial Applications

The emulsifier compositions according to the invention allow the production of particularly fine-droplet and stable emulsions. Accordingly, the present invention also relates to the use of the emulsifier compositions according to the invention in emulsions and to their use as a self-emulsifying base for the production of emulsions, more particularly in cosmetic and/or pharmaceutical preparations. In the context of the invention, the expression "self-emulsifying" means that the composition can be incorporated in final formulations without shearing, i.e. by simple mechanical mixing.

The emulsifier compositions according to the invention are particularly suitable for the production of PIT and microemulsions, preferably with a mean droplet size distribution of or smaller than, preferably smaller than, 1000 nm, preferably of or smaller than, preferably smaller than, 500 nm, more preferably of or smaller than, preferably smaller than 250 nm, and most preferably of or smaller than, preferably smaller than, 200 nm.

The particle size of emulsions can be visually determined by comparison with the particle size of standard emulsions. To determine the particle size of a standard emulsion, a diffraction pattern is produced by laser diffraction. The particle size distribution is then calculated from the light intensities of these diffraction patterns using the Fraunhofer theory (Sympatec Helos). The particle sizes can be determined with a Coulter® LS counter by dilution with water and then spraying the diluted emulsion into the counter.

The emulsifier compositions according to the invention are particularly suitable for the production of sprayable preparations.

The present invention also relates to a process for the production of sprayable emulsions in which (a) an emulsifier composition according to any of claims 1 to 6 is dispersed in an oil phase optionally containing other oil-soluble components and the dispersion is heated to a temperature above the phase inversion temperature, (b) an aqueous phase optionally containing water-soluble constituents is also heated to a temperature above the phase inversion temperature and (c) the oil phase and the aqueous phase are then cooled together with stirring to room temperature. There is no need to apply shear forces, simple mechanical stirring being sufficient.

The present invention also relates to cosmetic compositions containing 0.5 to 40% by weight and preferably 2.0 to 20% by weight of the emulsifier composition claimed in at least one of claims 1 to 6. Particularly preferred cosmetic compositions contain 0.5 to 40% by weight and preferably 2.0 to 20% by weight of the emulsifier composition claimed in at least one of claims 2 to 6. Preferably, the cosmetic compositions additionally contain at least one oil component liquid at 20° C. Particularly preferred cosmetic compositions contain (a) 0.5 to 40% by weight and preferably 2.0 to 20% by weight of the emulsifier composition claimed in at least one of claims 1 to 6, (b) 5 to 30% by weight of at least one oil component liquid at 20° C. and (c) water.

The present invention also relates to cosmetic preparations containing 0.5 to 40% by weight and preferably 2.0 to 20% by weight of the emulsifier composition claimed in at least one of claims 1 to 6 and at least one UV filter.

The present invention also relates to cosmetic preparations containing 0.5 to 40% by weight and preferably 2.0 to 20% by weight of the emulsifier composition claimed in at least one of claims 1 to 6 and at least one insect repellent.

The present invention also relates to cosmetic preparations containing 0.5 to 40% by weight and preferably 2.0 to 20% by weight of the emulsifier composition claimed in at least one of claims 1 to 6 and at least one self-tanning agent.

The present invention also relates to cosmetic preparations containing 0.5 to 40% by weight and preferably 2.0 to 20% by weight of the emulsifier composition claimed in at least one of claims 1 to 6 and at least one deodorizing component.

The cosmetic preparations according to the invention may be present in any of the forms known to the expert, such as creams, lotions, etc. In a preferred embodiment, the cosmetic preparations are present in the form of a sprayable formulation.

Oil Components

The preparations according to the invention contain an aqueous phase and an oil phase which may contain auxiliaries and additives. The percentage content of aqueous phase, including water-soluble active components, is typically in the range from 20 to 90% by weight, based on the composition as a whole, and the percentage content of oil phase typically in the range from 1 to 70% by weight, based on the composition as a whole. The oil phase may be made up of a single oil component or a mixture of oil components.

Suitable oil components are, for example, the classes of compounds mentioned in the following: Guerbet alcohols based on fatty alcohols containing 6 to 18 and preferably 8 to 10 carbon atoms, esters of linear or branched, saturated or unsaturated $C_{6-22}$ fatty acids with linear or branched, saturated or unsaturated $C_{6-22}$ fatty alcohols, more particularly 2-ethyl hexanol. The following are mentioned by way of example: hexyl laurate, myristyl isostearate, myristyl oleate, cetyl isostearate, cetyl oleate, stearyl isostearate, stearyl oleate, isostearyl myristate, isostearyl palmitate, isostearyl stearate, isostearyl isostearate, isostearyl oleate, oleyl myristate, oleyl isostearate, oleyl oleate, oleyl erucate, erucyl isostearate, erucyl oleate, cococaprylate/caprate. Other suitable esters are, for example, are esters of $C_{18-38}$ alkylhydroxycarboxylic acids with linear or branched, saturated or unsaturated $C_{6-22}$ fatty alcohols, esters of linear and/or branched, saturated or unsaturated fatty acids with polyhydric alcohols (for example propylene glycol, dimer diol or trimer triol) and/or Guerbet alcohols, triglycerides or triglyceride mixtures, liquid mono-, di- and triglyceride mixtures, esters of $C_{6-22}$ fatty alcohols and/or Guerbet alcohols with aromatic carboxylic acids, more particularly benzoic acid, esters of $C_{2-12}$ dicarboxylic acids with linear or branched, saturated or unsaturated alcohols containing 1 to 22 carbon atoms or polyols containing 2 to 10 carbon atoms and 2 to 6 hydroxyl groups, vegetable oils, branched primary alcohols, substituted cyclohexanes, linear dialkyl carbonates (for example Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Di-n-octyl Ether (Cetiol® OE) or ring opening products of epoxidized fatty acid esters with polyols, hydrocarbons, such as paraffin or mineral oils, oligo- or poly-α-olefins. According to the invention, dialkyl ethers, dialkyl carbonates, triglyceride mixtures and esters of $C_{8-24}$ fatty acids and $C_{8-24}$ fatty alcohols or mixtures of these substances are particularly suitable for use as the oil component. The dialkyl carbonates and dialkyl ethers may be symmetrical or asymmetrical, branched or unbranched, saturated or unsaturated and may be produced by reactions known from the prior art. Suitable silicone compounds are, for example, dimethyl polysiloxanes, methylphenyl polysiloxanes, cyclic silicones (cyclomethicone) and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

In a preferred embodiment of the invention, the oil component is selected from the group consisting of dialkyl carbonates and dialkyl ethers.

Particularly suitable dialkyl carbonates are compounds corresponding to formula (I):

$$R_2O(CH_2CH_2O)_n\text{—}CO\text{—}(OCH_2CH_2)_m\text{—}OR_2 \quad (I)$$

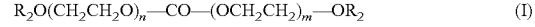

in which $R_1$ is a linear alkyl and/or alkenyl group containing 6 to 22 carbon atoms, a 2-ethylhexyl, isotridecyl or isostearyl group or a group derived from a polyol containing 2 to 15 carbon atoms and at least two hydroxyl groups, $R_2$ has the same meaning as $R_1$ or is a $C_1$-$C_5$ alkyl group and n and m independently of one another stand for 0 or numbers of 1 to 100.

Particularly suitable dialkylethers are compounds corresponding to general formula (II):

$$R_3\text{—}O\text{—}R_4 \quad (II)$$

in which $R_3$ and $R_4$ independently of one another represent a linear or branched alkyl and/or alkenyl group containing 6 to 22, preferably 6 to 12, preferably 16 to 22, preferably 8 to 18 and more particularly 12 to 18 carbon atoms. The ethers may be asymmetrical but are preferably symmetrical in structure.

Typical examples are di-n-octyl ether, di-i-octyl ether and di-n-stearyl ether. In a preferred embodiment, di-n-octyl ether (commercially obtainable under the name of Cetiol® OE) and/or di-i-octyl ether is used as the dialkyl ether.

A preferred embodiment of the invention are cosmetic preparations containing (a) 0.5 to 40, preferably 2.0 to 20% by weight of the emulsifier composition claimed in at least one of claims 1 to 6, (b) 5 to 30% by weight of at least one oil component liquid at 20° C. and (c) water, the at least one oil component liquid at 20° C. being selected from the group consisting of dialkyl carbonates and dialkyl ethers.

According to the invention, other suitable oil components are linear hydrocarbons with a chain length of 8 to 40 carbon atoms which may be branched or unbranched, saturated or unsaturated. Of these, branched, saturated $C_{8-40}$ alkanes are preferred. Both pure substances and mixtures may be used. The mixtures are normally mixtures of different isomeric compounds. Compositions containing $C_{10-30}$, preferably $C_{12-20}$ and more particularly $C_{16-20}$ alkanes are particularly suitable and, of these, a mixture of alkanes containing at least 10% by weight branched alkanes, based on the total quantity of alkanes, is particularly preferred. The alkanes are preferably branched, saturated alkanes. Mixtures of alkanes containing more than 1% by weight 5,8-diethyl dodecane and/or more than 1% by weight didecene are particularly suitable.

Providing they are liquid at 20° C., any oil components may be present as component c) of the cosmetic preparations according to the invention. If the oil components are not liquid at 20° C., they may be present as (additional) oil components in the cosmetic preparations.

Other Optional Auxiliaries and Additives

Depending on their intended application, the cosmetic formulations may contain a number of other auxiliaries and additives such as, for example, thickeners, superfatting agents, stabilizers, polymers, lecithins, phospholipids, biogenic agents, UV protection factors, antioxidants, deodorants, film formers, swelling agents, insect repellents, hydrotropes, solubilizers, preservatives, perfume oils, dyes, etc. which are listed by way of example in the following. The quantities in which the particular additives are used is determined by the intended use.

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, polyvinyl alcohol, polyvinyl pyrrolidone and bentonites such as, for example, Bentone® GeIVS-5PC (Rheox).

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor as described in EP 0693471 B1;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester;
- derivatives of benzophenone, preferably 2-hydroxy-4-methoxybenzo-phenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);
- propane-1,3-diones such as, for example, 1-(4-tert.butylphenyl)-3-(4'-methoxyphenyl)-propane-1,3-dione;
- ketotricyclo(5.2.1.0)decane derivatives as described in EP 0694521 B1.

Suitable water-soluble substances are

- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione and the enamine compounds described in DE 197 12 033 A1 (BASF) and also benzoic acid, 2-[4-(diethylamino)-2-hydroxybenzoyl]-, Hexyl Ester (Uvinul® A plus). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Particularly suitable broad-spectrum sun filters are 2,2'-methylene-bis-[4-(1,1,3,3-tetramethylbutyl)-6-(2H-benzotriazol-2-yl)-phenol] (Tinosorb M) and phenol-2,2'-[6(4-methoxyphenyl)-1,3,5-triazine-2,4-diyl]-bis[5-(2-ethylhexyl)-oxy]-(Tinosorb M).

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SOFW-Journal 122, 543 (1996) and in Parf. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to μmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorizing components counteract, mask or eliminate body odors. Body odors are formed through the action of skin bacteria on apocrine perspiration which results in the formation of unpleasant-smelling degradation products. Accordingly, suitable deodorizing components are inter alia germ inhibitors, enzyme inhibitors, odor absorbers or odor maskers. Suitable antiperspirant components are, for example, aluminium chlorohydrates, aluminium/zirconium chlorohydrates and zinc salts. These antiperspirants probably act by partially blocking the sweat glands through the precipitation of proteins and/or polysaccharides. Besides the chlorohydrates, aluminium hydroxylactates and acidic aluminium/zirconium salts may also be used. For example, an aluminium chlorhydrate which corresponds to the formula $[Al_2(OH)_5Cl].2.5H_2O$ and which is particularly preferred for the purposes of the invention is commercially available under the name of Locron® from Clariant GmbH. The aluminium/zirconium tetrachlorohydrex/glycine complexes marketed, for example, by Reheis under the name of Rezal® 36G are also preferably used in accordance with the invention. Other suitable deodorizing components are esterase inhibitors, preferably trialkyl citrates, such as trimethyl citrate, tripropyl citrate, triisopropyl citrate, tributyl citrate and, in particular, triethyl citrate (Hydagen® C.A.T., Cognis Deutschland GmbH). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in the compositions. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

Suitable insect repellents are, for example, N,N-diethyl-m-toluamide, pentane-1,2-diol or 3-(N-n-butyl-N-acetylamino)-propionic acid ethyl ester), which is marketed as Insect Repellent® 3535 by Merck KGaA, and Butylacetylaminopropionate.

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Suitable perfume oils are mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, and synthetic perfume compounds of the ester, ether, aldehyde, ketone, alcohol and hydrocarbon type, are also suitable.

Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810, quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

The cosmetic compositions are suitable for coating various substrates. The present invention also relates to the use of the compositions according to the invention, more particularly as conditioners, for coating nonwovens, woven fabrics, cosmetic and domestic wipes and to substrates coated with these compositions.

Examples of coated substrates are wipes for body care and personal hygiene, make-up removing wipes, coated cotton-wool pads, wipes coated with sun protection formulations or insect repellents, etc.

The invention is described herein with reference to specific embodiments. One of ordinary skill in the art, however, appreciates that various modifications and changes can be made without departing from the scope of the invention as set forth in the claims. Accordingly, the specification is to be regarded in an illustrative manner, rather than a restrictive view and all such modifications are intended to be included within the scope of the invention.

The following Examples relate to investigations of emulsions produced with the emulsifier compositions according to the invention in comparison with emulsions produced with other commercially available emulsifiers.

EXAMPLES

TABLE 1

Formulations 1-2 in Table 1 correspond to the invention; formulations C1-C3 are intended for comparison. The quantity data represent % by weight of the commercially available substances in the composition as a whole.

| Ingredients | C1 | C2 | C3 | 1 | 2 |
|---|---|---|---|---|---|
| Emulgade ® SE-PF | 5 | | | | |
| Eumulgin ® B1 | | 1.5 | 1.5 | 2.5 | 3.5 |
| Eumulgin ® B2 | | 1.5 | 1.5 | 0.5 | |
| Cutina ® MD | | | 3.0 | | |
| Cutina ® GMS-V | | 3.0 | | | |
| Cutina ® PES | | | | 3.0 | 2.5 |
| Cetiol ® OE | 5.0 | 5.0 | 5.0 | 5.0 | 5.0 |
| Cetiol ® LC | 5.0 | 5.0 | 5.0 | 5.0 | 5.0 |
| Glycerol | 3.0 | 3.0 | 3.0 | 3.0 | 3.0 |
| Water, preservative | to 100 | to 100 | to 100 | to 100 | to 100 |
| Phase stability at −5° C./RT/40° C. | | | | | |
| After 1 week | 1/5/5 | 5/5/5 | 5/5/5 | 1/1/1 | 1/1/1 |
| After 2 weeks | 1/5/5 | 5/5/5 | 5/5/5 | 1/1/1 | 1/1/1 |
| After 4 week | 1/5/5 | 5/5/5 | 5/5/5 | 1/1/1 | 1/1/1 |
| After 8 weeks | 1/5/5 | 5/5/5 | 5/5/5 | 1/1/1 | 1/1/1 |
| After 12 weeks | 1/5/5 | 5/5/5 | 5/5/5 | 1/1/1 | 1/1/1 |

RT = room temperature 20° C.
Legend:
Evaluation criteria for visual phase stability:
1 - stable; 2 - minimal separation; 3 - slight separation; 4 -distinct separation; 5 - separation

TABLE 2

Formulations 3-6 in Table 2 correspond to the invention. The quantity data represent % by weight of the commercially available substances in the composition as a whole.

| Ingredients | 3 | 4 | 5 | 6 |
|---|---|---|---|---|
| Eumulgin ® B1 | 3.5 | 3.5 | 3.5 | 3.5 |
| Cutina ® PES | 2.5 | 2.5 | 2.5 | 2.5 |
| Cetiol ® OE | | | | |
| Cetiol ® LC | 10 | | | |
| Cetiol ® 868 | | 10 | | |
| Cetiol ® CC | | | 10 | |
| Cetiol ® SN | | | | 10 |
| Glycerol | 3.0 | 3.0 | 3.0 | 3.0 |
| Water, preservative | to 100 | to 100 | to 100 | to 100 |
| Phase stability at −5° C./RT/40° C. | | | | |
| After 1 week | 1/1/1 | 1/1/1 | 1/1/1 | 1/1/1 |
| After 2 weeks | 1/1/1 | 1/1/1 | 1/1/1 | 1/1/1 |
| After 4 weeks | 1/1/1 | 1/1/1 | 1/1/1 | 1/1/1 |
| After 8 weeks | 1/1/1 | 1/1/1 | 1/1/1 | 1/1/1 |
| After 12 weeks | 1/1/1 | 1/1/1 | 1/1/1 | 1/1/1 |
| Macroscopic appearance at RT | | | | |
| 1 day after production | 1 | 1 | 1 | 1 |
| Microscopic appearance at RT | | | | |
| 1 day after production | 1 | 1 | 1 | 1 |

RT = room temperature 20° C.
Legend:
Evaluation criteria for visual phase stability:
1 - stable; 2 - minimal separation; 3 - slight separation; 4 -distinct separation; 5 - separation
Evaluation criteria for macroscopic appearance:
1 - bluish; 2 - blue-white; 3 - white; 4 - crystallization The patterns are evaluated after thermostatting to room temperature.

Evaluation Criteria for Microscopic Appearance:

1—average particle size $\leq$ 1 μm

2—average particle size 1-4 μm

3—average particle size 4-13 μm

4—average particle size 13-20 μm

5—average particle size 20-50 μm

The particle size of the test emulsion was visually compared with the particle size of standard emulsions. To determine the particle size of the standard emulsion, a diffraction pattern was produced by laser diffraction. The particle size distribution was then calculated from the light intensities of these diffraction patterns using the Fraunhofer theory (Sympatec Helos).

TABLE 3

Formulations 7 to 14 in Table 3 correspond to the invention. The quantity data represent % by weight of the commercially available substances in the composition as a whole.

| Ingredients | 7 | 8 | 9 | 10 | 11 | 12 | 13 | 14 |
|---|---|---|---|---|---|---|---|---|
| Eumulgin ® B1 | 3.5 | 2.9 | 3.5 | 3.5 | 3.5 | 3.5 | 3.5 | 3.5 |
| Eumulgin ® B2 |  | 1.0 |  |  |  |  |  |  |
| Cutina ® PES | 2.5 | 2.1 | 2.5 | 2.5 | 2.5 | 2.5 | 2.5 | 2.5 |
| Cetiol ® OE |  |  |  |  |  |  |  |  |
| Cetiol ® LC |  |  |  | 5.0 | 7.5 | 7.5 | 7.5 | 7.5 |
| Cetiol ® PGL | 10 | 10 |  |  |  |  |  |  |
| Eutanol ® G 16 |  |  | 5.0 |  |  |  |  |  |
| Myritol ® 331 |  |  |  | 2.5 |  |  |  |  |
| Cetiol ® B |  |  |  |  | 2.5 |  |  |  |
| Cetiol ® AB |  |  |  |  |  | 2.5 |  |  |
| Ethylhexylsalicylate |  |  |  |  |  |  | 2.5 |  |
| Octocrylene |  |  |  |  |  |  |  | 2.5 |
| Glycerol | 3.0 | 3.0 | 3.0 | 3.0 | 3.0 | 3.0 | 3.0 | 3.0 |
| Water, preservative | to 100 | to 100 | to 100 | to 100 | to 100 | to 100 | to 100 | to 100 |
| Phase stability at −5° C./RT/40° C. |  |  |  |  |  |  |  |  |
| After 1 week | 1/1/1 | 1/1/1 | 1/1/1 | 1/1/1 | 1/1/1 | 1/1/1 | 1/1/1 | 1/1/1 |
| After 2 weeks | 1/1/1 | 1/1/1 | 1/1/1 | 1/1/1 | 1/1/1 | 1/1/1 | 1/1/1 | 1/1/1 |
| After 4 weeks | 1/1/2 | 1/1/2 | 1/1/2 | 1/1/1 | 1/1/1 | 1/1/1 | 1/1/1 | 1/1/1 |
| After 8 weeks | 1/1/3 | 1/1/3 | 1/1/3 | 1/1/1 | 1/1/1 | 1/1/1 | 1/1/1 | 1/1/1 |
| After 12 weeks | 1/1/5 | 1/1/5 | 1/1/5 | 1/1/1 | 1/1/1 | 1/1/1 | 1/1/1 | 1/1/1 |
| Macr. appearance at RT |  |  |  |  |  |  |  |  |
| 1 day after production | 1 | 1 | 1 | 1 | 1 | 1 | 1 | 1 |
| Micr. appearance at RT |  |  |  |  |  |  |  |  |
| 1 day after production | 1-2 | 1-2 | 1 | 1 | 1 | 1 | 1 | 1 |

Macr. appearance = macroscopic appearance
Micr. appearance = microscopic appearance
RT = room temperature 20° C.
Legend:
Evaluation criteria for visual phase stability:
1 - stable; 2 - minimal separation; 3 - slight separation; 4 - distinct separation; 5 - separation
Evaluation criteria for macroscopic appearance:
1 - bluish; 2 - blue-white; 3 - white; 4 - crystallization The patterns are evaluated after thermostatting to room temperature.

Evaluation Criteria for Microscopic Appearance:
1—average particle size ≦ 1 μm
2—average particle size 1-4 μm
3—average particle size 4-13 μm
4—average particle size 13-20 μm
5—average particle size 20-50 μm The particle size of the test emulsion was visually compared with the particle size of standard emulsions. To determine the particle size of the standard emulsion, a diffraction pattern was produced by laser diffraction. The particle size distribution was then calculated from the light intensities of these diffraction patterns using the Fraunhofer theory (Sympatec Helos).

TABLE 4

Formulation 15 in Table 4 corresponds to the invention; formulation C4 is intended for comparison. The quantity data represent % by weight of the commercially available substances in the composition as a whole.

| Ingredients | C4 | 15 |
|---|---|---|
| Emulgade ® SE-PF | 7.8 |  |
| Eumulgin ® B1 |  | 4.5 |
| Eumulgin ® B3 | 5.2 | 5.2 |
| Cutina ® PES |  | 3.3 |
| Cetiol ® OE | 2.0 | 2.0 |
| Cetiol ® SN | 2.0 | 2.0 |
| Benzophenone-3 | 4.0 | 4.0 |
| Homosalat | 7.0 | 7.0 |
| Ethylhexyl Methoxycinnamate | 7.5 | 7.5 |
| Ethylhexyl Salicylate | 5.0 | 5.0 |
| Copherol ® F 1300 | 1.0 | 1.0 |
| Glycerol | 5.0 | 5.0 |
| Water, preservative | to 100 | to 100 |
| Phase stability at −5° C./RT/40° C. |  |  |
| After 1 week | 1/1/1 | 1/1/1 |
| After 2 weeks | 1/1/1 | 1/1/1 |
| After 3 weeks | 1/1/1 | 1/1/1 |
| Sensory evaluation of the RT patterns | 2 | 1 |

RT = room temperature 20° C.
Legend:
Evaluation criteria for visual phase stability:
1 - stable; 2 - minimal separation; 3 - slight separation; 4 - distinct separation; 5 - separation
Sensory evaluation criteria (10 volunteers)
1 - very high acceptance; 2 - average acceptance; 3 - unacceptable

Example 16

60% by weight Eumulgin B1
40% by weight Cutina PES

APPENDIX

1) Cetiol® AB—INCI: C12-15 Alkylbehzoate Manufacturer: Cognis Deutschland GmbH & Co. KG
2) Cetiol® B—INCI: Dibutyl Adipate Manufacturer: Cognis Deutschland GmbH & Co. KG
3) Cetiol® CC—INCI: Dicaprylyl Carbonate Manufacturer: Cognis Deutschland GmbH & Co. KG
4) Cetiol® LC—INCI: Coco-Caprylate/Caprat Manufacturer: Cognis Deutschland GmbH & Co. KG
5) Cetiol® OE—INCI: Dicaprylyl Ether Manufacturer: Cognis Deutschland GmbH & Co. KG
6) Cetiol® SN—INCI: Cetearyl Isononanoate Manufacturer: Cognis Deutschland GmbH & Co. KG
7) Cetiol® 868—INCI: Ethylhexyl Stearate Manufacturer: Cognis Deutschland GmbH & Co. KG
8) Cetiole PGL—INCI: Hexyldecanol+Hexyldecyl Laurate Manufacturer: Cognis Deutschland GmbH & Co. KG
9) Copherol® F 1300—INCI: Tocopherol Manufacturer: Cognis Deutschland GmbH & Co. KG
10) Cutina® MD—INCI: Glyceryl Stearat Manufacturer: Cognis Deutschland GmbH & Co. KG
11) Cutina® GMS-V—INCI: Glyceryl Stearat Manufacturer: Cognis Deutschland GmbH & Co. KG
12) Cutina® PES—INCI: Pentaerythrityl Distearat Manufacturer: Cognis Deutschland GmbH & Co. KG
13) Emulgade® SE-PF—INCI: Glyceryl Stearat, Ceteareth-20, Ceteareth-12, Cetearyl Alcohol, Cetyl Palmitat Manufacturer: Cognis Deutschland GmbH & Co. KG
14) Eumulgin® B1—INCI: Ceteareth-12 Manufacturer: Cognis Deutschland GmbH & Co. KG
15) Eumulgin® B2—INCI: Ceteareth-20 Manufacturer: Cognis Deutschland GmbH & Co. KG
16) Eumulgin® B3—INCI: Ceteareth-30 Manufacturer: Cognis Deutschland GmbH & Co. KG
17) Eutanol® G16—INCI: Hexyldecanol Manufacturer: Cognis Deutschland GmbH & Co. KG
18) Myritole 331—INCI: Cocoglycerides Manufacturer: Cognis Deutschland GmbH & Co. KG

What is claimed is:

1. An emulsifier composition, comprising:
    (a) an ester of a $C_{6-22}$ fatty acid and a polyol selected from the group consisting of pentaerythritol, dipentaerythritol, tripentaerythritol, and mixtures thereof;
    (b) at least one alkoxylated nonionic emulsifier; and
    (c) less than 10% by weight water,
wherein said emulsifier composition comprises less than about 10% by weight of partial glycerides, based on the amount of component (a) present in the composition, and wherein said alkoxylated nonionic emulsifiers are ethoxylated and/or propoxylated.

2. The emulsifier composition according to claim 1, wherein the ratio by weight of (a) to (b) ranges from about 20:80 to about 80:20.

3. The emulsifier composition according to claim 1, wherein component (a) is selected from the group consisting of $C_{6-22}$ fatty acid esters of pentaerythritol, $C_{6-22}$ fatty acid esters of dipentaerythritol, $C_{6-22}$ fatty acid esters of tripentaerythritol, and mixtures thereof, wherein component (a) has a melting point of at least 30° C.

4. The emulsifier composition according to claim 1, wherein component (a) comprises an ester mixture containing (i) 5 to 35% by weight monoester, (ii) 20 to 50% by weight diester, and (iii) 25 to 50% by weight triester.

5. The emulsifier composition according to claim 1, wherein component (a) comprises an ester mixture containing (i) 10 to 25% by weight monoester, (ii) 25 to 40% by weight diester, (iii) 30 to 45% by weight triester.

6. The emulsifier composition according to claim 1, wherein component (a) comprises an ester mixture containing (i) 12 to 19% by weight monoester, (ii) 25 to 35% by weight diester, (iii) 30 to 40% by weight triester, and (iv) 6 to 11% by weight tetraester.

7. The emulsifier composition according to claim 1, wherein component (b) is selected from the group consisting of $C_{12-24}$ fatty alcohol ethoxylates and mixtures of $C_{12-24}$ fatty alcohol ethoxylates.

8. A phase inversion temperature (PIT) emulsion or a microemulsion, comprising the emulsifier composition of claim 1, wherein the mean droplet size is not greater than 1000 nm.

9. An emulsion, comprising the emulsifier composition of claim 1.

10. A process for the production of an emulsion, comprising the steps of:
    (i) providing an emulsifier composition, comprising:
        (a) an ester of a $C_{6-22}$ fatty acid and a polyol selected from the group consisting of pentaerythritol, dipentaerythritol, tripentaerythritol, and mixtures thereof;
        (b) at least one alkoxylated nonionic emulsifier; and
        (c) less than 10% by weight water,
    wherein said emulsifier composition comprises less than about 10% by weight of partial glycerides, based on the amount of component (a) present in the composition;
    (ii) dispersing the emulsifier composition in an oil phase;
    (iii) heating the emulsifier composition dispersed in the oil phase to a temperature above the phase inversion temperature thereof;
    (iv) heating an aqueous phase to a temperature above the phase inversion temperature thereof; and
    (v) stirring the oil phase with the aqueous phase and cooling to room temperature,
    wherein said alkoxylated nonionic emulsifiers are ethoxylated and/or propoxylated.

11. A cosmetic composition, comprising:
    an emulsifier composition, comprising:
    (a) an ester of a $C_{6-22}$ fatty acid and a polyol selected from the group consisting of pentaerythritol, dipentaerythritol, tripentaerythritol, and mixtures thereof;
    (b) at least one alkoxylated nonionic emulsifier; and
    (c) less than 10% by weight water,
wherein said emulsifier composition comprises less than about 10% by weight of partial glycerides, based on the amount of component (a) present in the emulsifier composition, and wherein the emulsifier composition is present in the cosmetic composition in an amount of from about 0.5 to about 40% by weight of the cosmetic composition, and wherein said alkoxylated nonionic emulsifiers are ethoxylated and/or propoxylated.

12. The cosmetic composition according to claim 11, wherein the emulsifier composition is present in the cosmetic composition an amount of from about 2 to about 20% by weight of the cosmetic composition.

13. The cosmetic composition according to claim 11, further comprising at least one oil component which is liquid at 20° C.

14. The cosmetic composition according to claim 11, comprising:
   about 0.5 to about 40% by weight of the emulsifier composition;
   about 5 to about 30% by weight of at least one oil component which is liquid at 20° C.; and
   water.

15. The cosmetic composition according to claim 11, comprising:
   about 2.0 to about 20% by weight of the emulsifier composition;
   about 5 to about 30% by weight of at least one oil component which is liquid at 20° C.; and
   water.

16. The cosmetic composition according to claim 11, coated onto a substrate.

17. The cosmetic composition according to claim 16, wherein the substrate is selected from the group consisting of nonwovens, woven fabrics, cosmetic wipes, and household wipes.

18. The emulsifier composition of claim 1, wherein said partial glycerides are present in an amount of about 1 to about 3% by weight, based on the amount of component (a) in the composition.

19. The emulsifier composition of claim 1, wherein said partial glycerides are present in an amount of less than about 1% by weight, based on the amount of component (a) in the composition.

20. The emulsifier composition of claim 1, which is free of partial glycerides.

* * * * *